United States Patent
Epshtein et al.

(10) Patent No.: US 8,524,229 B2
(45) Date of Patent: Sep. 3, 2013

(54) MEDICAMENT AND A METHOD FOR REGULATION OF THE VASCULAR TONE

(75) Inventors: Oleg Illich Epshtein, Moscow (RU); Andrey Vasilevich Martyushev, Moscow (RU)

(73) Assignee: Oleg I. Epshtein (RU)

( * ) Notice: Subject to any disclaimer, the term of this patent is extended or adjusted under 35 U.S.C. 154(b) by 0 days.

(21) Appl. No.: 13/547,737

(22) Filed: Jul. 12, 2012

(65) Prior Publication Data

US 2012/0282265 A1      Nov. 8, 2012

Related U.S. Application Data

(62) Division of application No. 10/499,072, filed as application No. PCT/RU02/00385 on Aug. 13, 2002, now Pat. No. 8,241,625.

(30) Foreign Application Priority Data

Dec. 26, 2001   (RU) ................................ 2001135015

(51) Int. Cl.
*A61K 39/395*     (2006.01)

(52) U.S. Cl.
USPC ........................................................ 424/130.1

(58) Field of Classification Search
None
See application file for complete search history.

(56) References Cited

U.S. PATENT DOCUMENTS

2012/0251584 A1 * 10/2012 Epshtein et al. .............. 424/400

OTHER PUBLICATIONS

Sarikonda et al., 2009, J. Amer. Soc. of Hypertension 3: 158-165.*

* cited by examiner

*Primary Examiner* — Ilia Ouspenski
(74) *Attorney, Agent, or Firm* — Pergament Gilman & Cepeda LLP

(57) ABSTRACT

The method of treatment for diseases accompanied by disturbances of the vascular tone utilizes the use of ultra low doses of antibodies to a protein or a peptide involved in the vascular tone regulation or mediating the effects of other regulators; these antibodies are used in activated form produced by multiple subsequent dilution and external impact.

9 Claims, No Drawings

MEDICAMENT AND A METHOD FOR REGULATION OF THE VASCULAR TONE

This application is a Divsional of U.S. patent application Ser. No. 10/499,072 filed Oct. 30, 2009, which claims the benefit of International Application No. PCT/RU2002/00385, filed Aug. 13, 2002, and Russian Federation Application No. 2001135015, filed on Dec. 26, 2001, all of which are hereby incorporate herein by reference in their entireties.

FIELD OF THE INVENTION

The invention belongs to the field of medicine and can be utilized to normalize the vascular tone and prevent acute and chronic illnesses accompanied by disturbances of the vascular tone, primarily in the arteries.

BACKGROUND

The art includes use of antibodies in the treatment of pathological syndromes (SU 1331508 A, A 61 K 39/00, 1984; SU 1730144 A1, C 12 N 7/00, 1992).

Medications such as sera and immunoglobulins based on antibodies in therapeutic concentrations, have also been described (e. g., see "Register of remedies used in Russia. The encyclopaedia of remedies", 7th edition, 2000, pp.358-359 (in Russian)).

None of the mentioned medications, however, are used in the treatment of diseases characterized by disturbances of the vascular tone.

There has been described a method of treating diseases accompanied by disturbances of the vascular tone through administration of substances specifically interacting with endogenous factors involved in the vascular tone regulation (e. g., see "Register of remedies used in Russia. The encyclopaedia of remedies", 7th edition, Moscow, RLS, 2000, pp.178, 406 (in Russian)). The most important disadvantage of such medications is their adverse effects.

DESCRIPTION OF THE INVENTION

The invention is aimed at producing an effective and safe medicament for treatment and prevention of diseases accompanied by disturbances of the vascular tone (primarily in the arteries), wherein activated (potentiated) antibodies are used.

This task is solved by the presence in the medicament of ultra low doses of monoclonal, polyclonal, immune or natural antibodies to a protein or a peptide involved in the vascular tone regulation or mediating the effects of other regulators; these antibodies are used in activated (potentiated) form produced by multiple subsequent dilution and external impact, primarily in accordance with homeopathic technology.

The method of treatment for diseases accompanied by disturbances of the vascular tone, primarily in the arteries, presents the use of antibodies to a protein or a peptide involved in the vascular tone regulation or mediating the effects of other regulators; these antibodies are used in activated form produced by multiple subsequent dilution and external impact.

The use of a mixture of different, preferably centesimal, homeopathic dilutions is most beneficial.

Experiments have been carried out to prove that the administered activated (potentiated) antibodies to a protein or a peptide involved in the vascular tone regulation exert a modifying, instead of inhibiting, effect on physiological and pathological processes mediated or regulated by this protein or peptide; the latter is responsible for the therapeutic efficiency of the medication presented.

The medication produced in accordance with the invention presents a new pharmacological preparation characterized by the presence of specific pharmacological activity, the absence of adverse effects as well as drug tolerance and dependence; by ecological purity and a low prime cost.

VARIANTS OF THE INVENTION IMPLEMENTATION

The drug preparation is produced as follows.

To treat a disease or a pathological syndrome caused or accompanied by disturbances of the vascular tone, clinical experiments are used to discover a protein or peptide regulating the vascular tone, which alterations characterize this disease or accompany its development.

Biochemical methods are used to separate this peptide or protein. Thereafter, the whole protein or its fragment (not less than 3 amino acids) is utilized as an immunogen in the immunization of laboratory animals and producing immune antibodies, or in a hybridizomatechnology to produce monoclonal antibodies. The antibodies produced are purified by affinity chromatography.

The technique of immune and monoclonal antibody production is described, for example, in: Immunological methods (Ed.by H.Friemel), Moscow, Medicine publishers, 1987, pp.9-23 (book in Russian).

Multiple subsequent dilutions and external impact, usually mechanical, are exerted on the isolated antibodies until ultra low or low doses are produced, e. g., preferably in accordance with homeopathic technology of potentiation (dynamization) (see V. Shvabe, Homeopathic Pharmaceutical Agents. A Manual on Description and Preparation, Moscow, 1967, p.12-38). (In Russian)). To do so, a uniform concentration reduction is employed wherein 1 volume unit of the antibodies is diluted in 9 volume units (for a decimal dilution D) or in 99 volume units (for a centesimal dilution C) of a neutral diluent with multiple vertical shaking of every dilution; for the most part, separate containers are used for every subsequent dilution until the needed concentration (potency) is reached.

External impacts in the concentration reduction process can also include ultrasound, electromagnetic or other physical influences.

The medication thus prepared is utilized preferably in common homeopathic dosage forms and dilutions, in alcohol or aqueous solutions or tablets (granules) prepared by impregnation until saturation of the excipient with a potentiated solution or by direct instillation of the latter into a liquid dosage form. To enhance the therapeutic effect of the preparation, a mixture of different homeopathic dilutions is employed.

EXAMPLES

Example I

An experimental study was performed to evaluate the effect of antibodies to angiotensin II receptor (Anti-R-angiotensin II-c), activated forms of ultra low doses, on blood pressure in ISIAH strain rats with hereditary arterial hypertension. Blood pressure in the caudal artery was measured after 5 days of peroral administration of potentiated polyclonal rabbit antibodies against the C-terminal fragment of the human angiotensin II receptor, antibodies being employed in a mixture of homeopathic dilutions C12-C30+C200 (0.5 ml of water solution).

The blood pressure figures before and after drug administration are presented in Table 1.

TABLE 1

Effect of Anti-R-angiotensin-II-c on blood pressure in hypertensive ISIAH strain rats.

| # | Rat # | Baseline blood pressure (average of 3 measurements) | Blood Pressure after 5 days of treatment | Decrease in Blood pressure (3)-(4) | Blood Pressure after subsequent 7 days without medication | Increase in Blood pressure (6)-(4) | Blood Pressure after second 5-day treatment course | Decrease in blood pressure (6)-(8) |
|---|---|---|---|---|---|---|---|---|
| 1 | 2 | 3 | 4 | 5 | 6 | 7 | 8 | 9 |
| 1 | 31 | 175 | 151 | 24 | 166 | 15 | 150 | 16 |
| 2 | 32 | 184 | 163 | 21 | 186 | 23 | 170 | 16 |
| 3 | 33 | 186 | 169 | 17 | 165 | −4 | 150 | 15 |
| 4 | 4 | 171 | 165 | 6 | 189 | 24 | 170 | 19 |
| 5 | 34 | 187 | 172 | 15 | 190 | 18 | 175 | 15 |
| 6 | 10 | 181 | 166 | 15 | 185 | 19 | 170 | 15 |
| 7 | 11 | 171 | 162 | 9 | 169 | 7 | 155 | 14 |
| 8 | 38 | 182 | 160 | 22 | 185 | 25 | 165 | 20 |
| 9 | 16 | 180 | 169 | 11 | 183 | 14 | 165 | 18 |
| 10 | 19 | 186 | 166 | 20 | 186 | 20 | 170 | 16 |
| | X ± m | 180 + 1.91 | 164 + 1.86 | 16 ± 1.88 | 180 ± 3.08 | 16.1 ± 2.81 | 164 ± 2.87 | 16.4 ± 0.62 |

The data in the table show that the medication exerts a hypotensive effect.

Example 2

An experimental study was performed to evaluate the effect of antibodies to angiotensin II (activated forms of ultra low doses) on blood pressure in ISIAH strain rats with hereditary arterial hypertension. Blood pressure in the caudal artery was measured after 5 days of peroral administration of potentiated monoclonal antibodies to angiotensin II employed in a mixture of homeopathic dilutions C12+C30+C200 (0.5 ml of water solution).

The blood pressure figures before and after drug administration are given in Table 2.

TABLE 2

| Rat # | Baseline blood pressure | Blood pressure 3 hours after a single shot | Blood pressure after 5 days of treatment | Change in blood pressure after a single shot ((3) − (2) difference) | Change in blood pressure after 5 days of treatment ((4) − (2) difference) |
|---|---|---|---|---|---|
| 1 | 2 | 3 | 4 | 5 | 6 |
| 11 | 200 | 167 | 161 | −33 | −39 |
| 12 | 189 | 150 | 189 | −39 | 0.0 |
| 16 | 200 | 189 | 160 | −11 | −40 |
| 19 | 167 | 178 | 144 | 11 | −23 |
| 21 | 211 | 189 | 167 | −22 | −44 |
| 22 | 178 | 167 | 205 | −11 | 27 |
| 23 | 189 | 167 | 205 | −22 | 16 |
| 27 | 178 | 194 | 200 | 16 | 22 |
| 28 | 178 | 172 | 144 | −6 | −34 |
| 30 | 189 | 178 | 178 | −11 | −11 |
| Mean + SEM | 187.9 ± 4.16 | 175.1 ± 4.21 | 175.3 ± 7.48 | −12.8* ± 5.49 | −12.6 ± 8.65 |

*($p < 0.05$)

The data in this table present a pronounced hypotensive effect of the medication.

Example 3

An experimental study was performed to evaluate the effect of antibodies to angiotensin I (activated forms of ultra low doses) on blood pressure in ISIAH strain rats with hereditary arterial hypertension. Blood pressure in the caudal artery was measured after 5 days of peroral administration of potentiated polyclonal mouse antibodies to angiotensin I employed in a mixture of homeopathic dilutions D6+C12+C200 (0.5 ml of water solution).

The blood pressure figures before and after drug administration are presented in Table 3.

TABLE 3

| Parameter | Baseline blood pressure | Blood pressure 3 hours after a single dose | Blood pressure after 5 days of treatment | Change in blood pressure after a single dose ((3) − (2) difference) | Change in blood pressure after 5 days of treatment ((4) − (2) difference) |
|---|---|---|---|---|---|
| Mean + SEM | 189.0 ± 4.1 | 178.1 ± 5.3 | 175.8 ± 8.2 | −10.9* ± 5.9 *($p < 0.05$) | −13.2 ± 8.5 |

The data in the table show that the medication exerts a hypotensive effect.

Example 4

Patient D., 50 years old, presented with a 10-year history of essential hypertension. On clinical and instrumental examination, he was diagnosed with "essential hypertension with primary heart involvement, $2^{nd}$ degree, myocardial hypertrophy of the left ventricle". He was administered polyclonal rabbit antibodies against the C-terminal fragment of the angiotensin II receptor (a mixture of homeopathic dilutions C12+C30+C200), I tablet BID. The blood pressure stabilized at 130-135/85 mm Hg within 7 days of the start of treatment. After 2 months of treatment, electrocardiography revealed a decrease in the myocardial hypertrophy and overload of the left ventricle.

Example 5

Patient Z., 50 years old, had a 10-year history of essential hypertension with primary kidney involvement. Prior to the start of antihypertensive treatment, her blood pressure was as high as 180/110 mm Hg. On clinical interview, she complained of headaches, edema, and fatigue. After the conventional antihypertensive measures had proved to be ineffective, she was administered monoclonal antibodies against the angiotensin II receptor (a mixture of homeopathic dilutions C12+C30+C200) and monoclonal antibodies against angiotensin II (a mixture of homeopathic dilutions D12+C30+LM2), 1 tablet BID. After 7 days of treatment, the patient reported an increase in energy levels, subsidence of the edema, and a stable blood pressure decrease to 140/95 mm Hg. After 2 months of treatment, blood pressure levels stabilized at 130/90 mm Hg, proteinuria went down from 0.3 g/l to 0.06 g/l.

Example 6

Patient V., 42 years old, had suffered from moderate Cushing's disease for 5 years. To treat her pronounced hypertension (up to 175/100 mm Hg), she was administered a compound preparation containing the following: polyclonal rabbit antibodies against the angiotensin II receptor (a mixture of homeopathic dilutions C12+C30+C200) and monoclonal antibodies against adrenocorticotropin (a mixture of homeopathic dilutions C12+C30+C200), 1 tablet TID. After 2 weeks of treatment, her blood pressure fell to 140/90 mm Hg, she was generally feeling better. After I month of treatment, serum ACTH levels decreased from 200 to 130 pg/ml, the body mass index went down from 37 to 35 $kg/m^2$. The patient was advised to go on with the treatment.

Example 7

Patient N., 52 years, diagnosed with "coronary artery disease, angina of effort, functional class 3; peripheral atherosclerotic disease of the lower extremities". This patient was administered activated polyclonal rabbit antibodies against the C-terminal fragment of human endothelial NO synthase (type III nitrogen oxide synthase) as a monotherapy, in a mixture of homeopathic dilutions C12+C30+C200, 1 tablet 3 TID, After 7 days of treatment, the patient noticed an improvement in exercise tolerance and general health. Pain in the lower extremities on fast walking appeared within 30 to 40 minutes (instead of 10 to 15 minutes prior to treatment). After 3 weeks of treatment, ECG showed an improvement in left ventricular myocardial ischemia and class 2 angina of effort.

Example 8

Patient 0., 67 years old, suffered from hypertension and decompensated type II diabetes mellitus. She had been having heart failure symptoms (cardiac asthma, congestive rales in the lungs) for 2 years and peripheral edema in the lower extremities for 2 months. In view of inefficiency of conventional treatment, she was administered a compound including activated monoclonal antibodies against tumor necrosis factor alpha (TNF-α) (a mixture of homeopathic dilutions C12+C30+C200) and activated antibodies against the TNF-α receptor (a mixture of homeopathic dilutions D12+LM10), 1 tablet BID. After 10 days of treatment, the heart failure improved, the peripheral edema was gone, there were no signs of pulmonary congestion, the patient was feeling better. The insulin dosage enough to control glycemia fell from 40 to 20 IU per day.

Example 9

Patient D., 62 years old, suffered from circulatory encephalopathy clue to atherosclerosis with predominant involvement of the cerebral arteries. He had a history of multiple transient ischemic attacks (TIAs) and presented with an ongoing attack accompanied by right-side hemiparesis and aphasia. The patient was given polyclonal antibodies against endothelial nitrogen oxide synthase (a mixture of homeopathic dilutions C12+C30+C200), 1 tablet dissolvable in the mouth every 30 minutes. After 4 hours of treatment, TIA symptoms (vertigo, tinnitus, weakness in the right arm, aphasia) showed signs of subsidence. Within 12 hours of the start of treatment, the attack was completely overcome.

Example 10

Patient M., 32 years old, had Raynaud's phenomenon secondary to a connective tissue disorder. Because of the worsening condition, she was administered monoclonal antibodies against endothelial nitrogen oxide synthase (a mixture of homeopathic dilutions C12+C30+C200), 1 tablet TID. After 7 days of treatment, the patient noticed that attacks precipitated by exposure of the extremities to cold had become less frequent, less painful and shorter. The patient was advised to continue the treatment.

Example 11

Patient V., 19 years old. She was evaluated for headaches and vertigo, and diagnosed. with hypotensive neurocirculatory asthenia (blood pressure 80/60 mm Hg). The patient was administered monoclonal antibodies against angiotensin I (a mixture of homeopathic dilutions C12+C30+C200) combined with activated angiotensin I (a mixture of homeopathic dilutions C12+C30+C200), 1 tablet TID. After 2 weeks of treatment, blood pressure stabilized at 100/80 mm Hg, the headaches had subsided and become less frequent.

Example 12

Patient 0., 42 years old. On examination at the Labour Medicine Research Institute, he was diagnosed with vibration disease, $2^{nd}$ stage localized variant. Due to the angiospastic syndrome accompanied by vegetosensory polyneuropathy and skin atrophy, which was resistant to conventional treatment, the patient was administered polyclonal rabbit antibodies against endothelin-1 (a mixture of homeopathic dilutions C12+C30+C200) combined with monoclonal antibodies against bradykinin (a mixture of homeopathic dilutions D6+C30+LM2), 1 tablet TID. After 10 clays of treatment, the angiospastic syndrome improved, which was also shown on capillaroscopy. After 2 months of treatment, the polyneuropathy and skin atrophy significantly subsided. The patient was advised to continue the treatment.

The invention claimed is:

1. A method of treating hypertension comprising administering a homeopathically potentized form of at least one antibody to angiotensin receptor.

2. The method of claim 1 wherein said antibody is selected from monoclonal, polyclonal or natural antibodies.

3. The method of claim 1 wherein said antibody to angiotensin receptor is to the angiotensin II receptor.

4. The method of claim 1 wherein said antibody to angiotensin receptor is to the angiotensin I receptor.

5. The method of claim 1 wherein said antibody to angiotensin receptor is to the C-terminal fragment of the angiotensin II receptor.

6. The method of claim 1, wherein said homeopathically-potentized form comprises one or more homeopathic dilutions.

7. The method of claim 6, wherein said one or more homeopathic dilutions comprises one or more centesimal homeopathic dilutions.

8. The method of claim 6, wherein said one or more homeopathic dilutions comprises C12, C30, and C200 homeopathic dilutions.

9. The method of claim 6, wherein said one or more homeopathic dilutions comprises D6, C12, and C200 homeopathic dilutions.

\* \* \* \* \*